United States Patent [19]
Cricchio et al.

[11] 4,234,485
[45] Nov. 18, 1980

[54] PROCESS FOR PREPARING 4-DESOXY-THIAZOLO[5,4-C]RIFAMYCIN DERIVATIVES

[75] Inventors: Renato Cricchio, Varese; Marisa Berti, Milan, both of Italy

[73] Assignee: Gruppo Lepetit S.p.A., Milan, Italy

[21] Appl. No.: 88,977

[22] Filed: Oct. 29, 1979

Related U.S. Application Data

[62] Division of Ser. No. 21,866, Mar. 19, 1979.

[30] Foreign Application Priority Data

Apr. 27, 1978 [IT] Italy .................. 22738 A/78

[51] Int. Cl.³ .................. C07D 51/20; A61K 31/425
[52] U.S. Cl. .................. 260/239.3 P; 424/270
[58] Field of Search .................. 260/239.3 P

[56] References Cited

U.S. PATENT DOCUMENTS

| | | | |
|---|---|---|---|
| 4,042,633 | 8/1977 | White et al. | 424/117 |
| 4,116,957 | 9/1978 | Rossetti et al. | 260/239.3 P |
| 4,129,562 | 12/1978 | Cricchio | 260/239.3 P |
| 4,144,234 | 3/1979 | Cricchio | 260/239.3 P |

*Primary Examiner*—Henry R. Jiles
*Assistant Examiner*—Robert T. Bond

[57] ABSTRACT

Novel 4-desoxy-thiazole[5,4-c]rifamycin derivatives of formula I wherein R stands for a group $-OR_1$, $-NR_2R_3$ or $-NHCOR_4$ wherein $R_1$ represents alkyl, alkenyl, alkynyl, cycloalkyl, aryl or aralkyl, $R_2$ and $R_3$ are independently selected from hydrogen, alkyl, alkenyl, alkynyl, cycloalkyl, aryl and aralkyl or $R_2$ and $R_3$ taken together with the adjacent nitrogen atom may represent a 5 to 7 membered heterocyclic ring and $R_4$ is a radical selected from the group consisting of alkyl, alkenyl, alkynyl, cycloalkyl, aryl and aralkyl; $R_5$ is hydrogen or acetyl; and a process for preparing them.

The novel compounds have an antibacterial utility.

4 Claims, No Drawings

PROCESS FOR PREPARING 4-DESOXY-THIAZOLO[5,4-C]RIFAMYCIN DERIVATIVES

This is a divisional of application Ser. No. 021,866 filed Mar. 19, 1979.

BACKGROUND OF THE INVENTION

In the prior art and more particularly in Belgium Pat. Nos. 832921 and 855153 the class of compounds thiazolo[5,4-c]rifamycins are described which bear a hydrogen atom on the 2 bond-positioned carbon atom of the thiazole ring (i.e. rifamycin P). While the former patent describes the novel compound and a method for producing it by fermenting *Nocardia mediterranea* strains ATCC 31064, 31065 and 31066, the latter relates to a process for preparing rifamycin P and rifamycin Q, the corresponding 2'-hydroxymethyl derivative, by condensing rifamycin S with a cysteine ester and then decarboxylating or reducing the obtained intermediate. Moreover, some condensation products of rifamycin S with cysteine esters, amides or hydrazides, i.e. thiazolorifamycins characterized by a carbalkoxy, carbamyl or hydrazinocarbonyl group on the 2'-positioned carbon atom, are known from German Offenlegungsschrift No. 2720113.

DESCRIPTION OF THE PREFERRED EMBODIMENTS

The present invention is concerned with 4-desoxy-thiazolo-[5,4-c]rifamycin derivatives of the general formula I

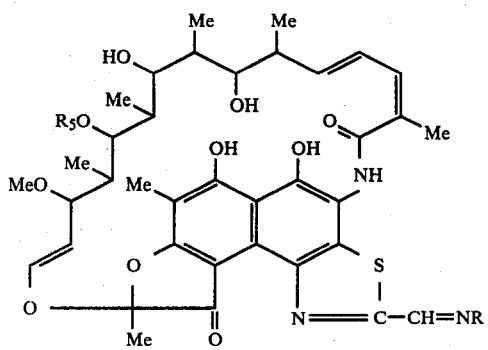

wherein R stands for a group $-OR_1$, $-NR_2R_3$, or $-NHCOR_4$ wherein $R_1$ represents alkyl, alkenyl, alkynyl, cycloalkyl, aryl or aralkyl, $R_2$ and $R_3$ are independently selected from hydrogen, alkyl, alkenyl, alkynyl, cycloalkyl, aryl and aralkyl, or $R_2$ and $R_3$ taken together with the adjacent nitrogen atom may represent a 5 to 7 membered hererocyclic ring and $R_4$ is a radical selected from the group consisting of alkyl, alkenyl, alkynyl, cycloalkyl, aryl and aralkyl, $R_5$ is hydrogen or acetyl. As used herein, the term "alkyl" and the "alkyl" portion in the other hereinlisted substituents containing an aliphatic saturated moiety, identifies straight or branched radicals having from 1 to 8 carbon atoms, which can be unsubstituted or contain one or more substituents on the carbon chain such as halogen atoms, amino, mono- and di-$(C_1-C_4)$alkylamino, $(C_1-C_4)$alkoxy, $(C_5-C_8)$cycloalkoxy, phenoxy, phenyl-$(C_1-C_4)$alkoxy, nitro, cyano, hydroxy, carboxy, carbo$(C_1-C_4)$alkoxy and carbamoyl.

The terms "alkenyl" and "alkynyl" refer to straight or branched radicals having at most 8 carbon atoms which may contain one or a plurality of double and triple bonds respectively.

The expression "cycloalkyl" designates a cycloaliphatic ring containing from 5 to 8 carbon atoms which may optionally bear one or two $(C_1-C_4)$alkyl substituents.

The term "aryl" and the "aryl" portion of the other hereinlisted substituents containing an aromatic moiety, identifies a benzene rest which can be unsubstituted or bear one or more substituents selected from halo, $(C_1-C_4)$alkyl, halo-$(C_1-C_4)$alkyl, $(C_1-C_4)$alkenyl, $(C_5-C_8)$cycloalkyl, amino, mono- and di-$(C_1-C_4)$alkylamino, $(C_1-C_4)$alkoxy, methylenedioxy, cyano, carboxy, hydroxy, carbo-$(C_1-C_4)$alkoxy, carbamoyl and nitro.

The expression "5 to 7 membered heterocyclic ring" includes also compounds having a further heteroatom selected from oxygen, nitrogen and sulfur and bearing $(C_1-C_4)$alkyl or $(C_4-C_7)$cycloalkyl substituents such as, for instance, pyrrolidine, pyrazolidine, piperidine, piperazine, 4-methyl-piperazine, 4-cyclopentylpiperazine, 4-cyclopropylpiperazine, morpholine and thiazolidine. In the structure formulas "Me" identifies the methyl group.

The novel compounds of the present invention are prepared by a process which, starting from rifamycin S or its 25-desacetyl derivative of formula II

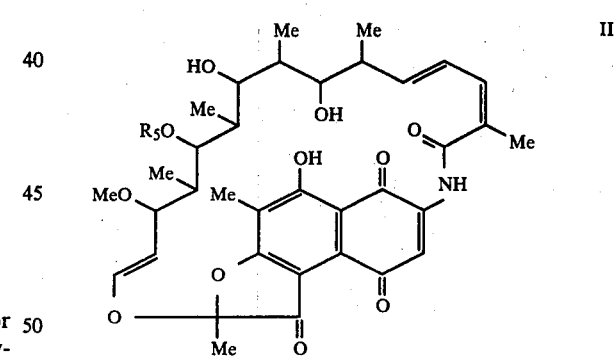

wherein $R_5$ is hydrogen or acetyl, a cysteine derivative of formula III

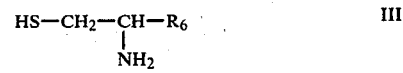

wherein $R_6$ stands for $-H$ or $-COOH$, and a compound of formula IV

wherein R is as defined before, runs through the following scheme:

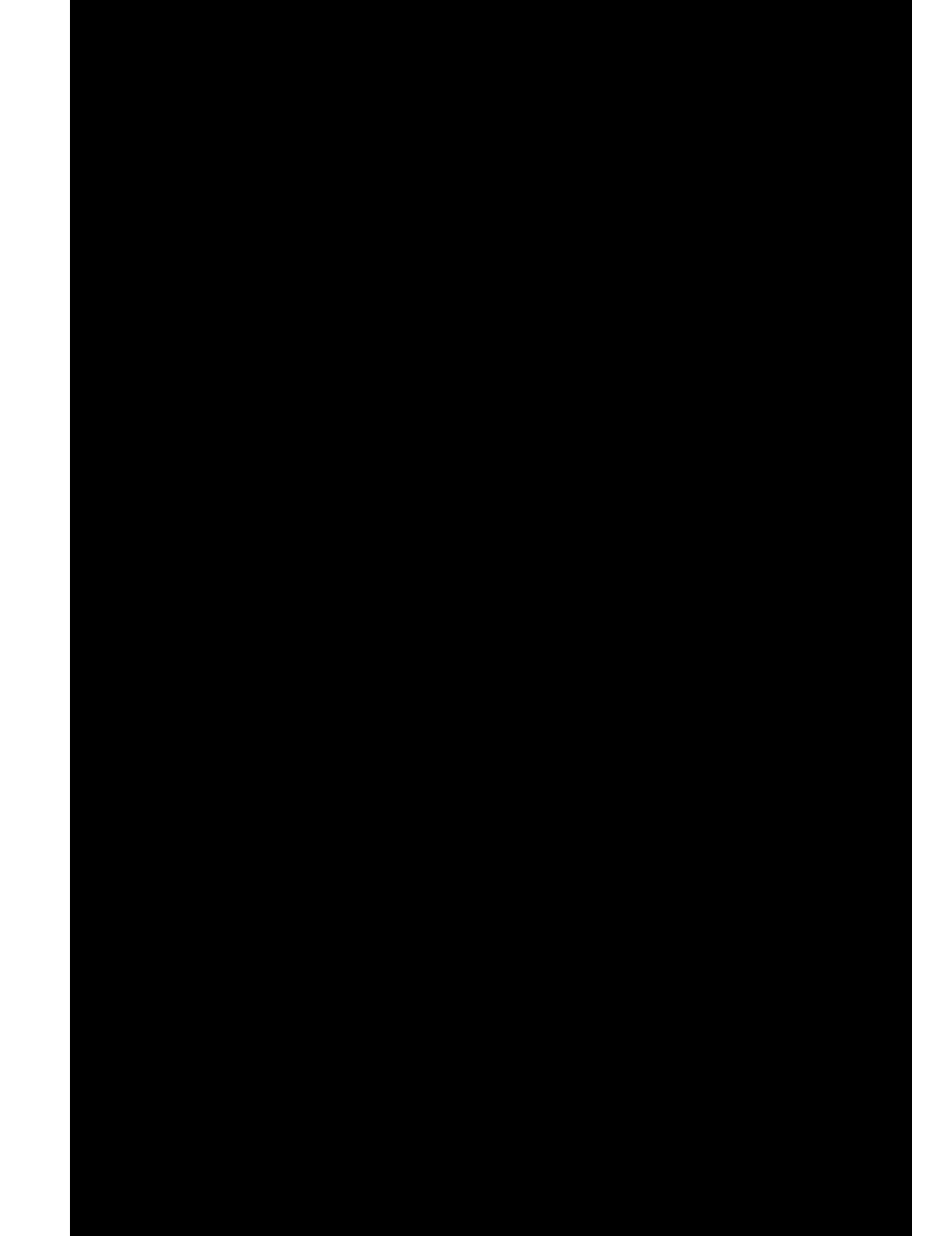

eliminate the resulting hydroquinone derivative by re-oxidation to the original quinone and simultaneous extraction of this latter with a proper solvent. Once the reaction side-products have been eliminated, the thiazolorifamycin I may be easily recovered as a crystalline product by following usual techniques.

Alternatively the reaction outlined in the above scheme may be carried out in a single step by reacting about equimolar proportions of the starting compounds II, III and IV in a water-miscible organic solvent in the presence of at least the stoichiometric amount of a suitable oxidizing agent which does not unfavourably interfer with the reactants, such as for instance a tetrasubstituted quinone or rifamycin S itself. Also in this case the reaction course is followed by thin layer chromatography (eluting with CHCl₃:MeOH 9:1) which shows the disappearance of the starting rifamycin S and the presence of a yellow fluorescent spot due to the novel thiazolorifamycin of formula I. Generally as for the recovery of the end products the same procedure used in the two-step process can be advantageously followed.

The compounds of the present invention have an antibacterial utility. More particularly they possess an outstanding biological activity against gram-positive and gram-negative strains as well as mycobacteria when used in an effective antimicrobial amount. An effective antimicrobial amount refers to that amount of the active compound which will inhibit or kill a microbe upon contact. Contacting the microbe may be in vitro as on a non-living substrate, or in vivo, as in the treatment of an infection in an animal. As for the in vitro activity, the hereinbelow reported table shows the minimal inhibitory concentrations (MIC), expressed as μg/ml, of some representative members of the compounds of the invention:

| Strain | Compound of example No. | | | |
|---|---|---|---|---|
| | 1 | 2 | 3 | 4 |
| Staph. aureus | 0.0008 | 0.00078 | 0.003 | 0.00078 |
| Staph. aureus Tour | 0.003 | 0.003 | 0.006 | 0.001 |
| Strept. haemolyticus | 0.006 | 0.01 | 0.01 | 0.006 |
| Strept. faecalis | 0.025 | 0.006 | 0.01 | 0.003 |
| Dipl. pneumoniae | 0.006 | 0.006 | 0.003 | 0.006 |
| Proteus vulgaris | 0.8 | 6.25 | 6.25 | 3.12 |
| Escherichia coli | 12.5 | 12.25 | 6.25 | 12.5 |
| Kleb. pneumoniae | 25 | 25 | 12.5 | 25 |
| Pseud. aeruginosa | 6.25 | 25 | 25 | 12.5 |
| Myc. Tub. H₃₇Rv | 0.30 | 0.60 | 0.62 | 0.31 |

The need of new antibiotics is practically unending, since the pathogenic microorganisms are capable of aquiring resistance to several families of widely employed antibiotics. This fact has been confirmed by many scientists in the microbiological field. See for instance Chem. Eng. News of Sept. 25, 1978, page 27, left column.

The rifamycin derivatives of the present invention also are effective in inhibiting at low concentration the growth of microorganisms which are resistant to other known antibiotics and possess an outstanding in vivo activity against experimental infection by *Staphylococcus aureus* both when administered per os and subcutaneously.

For instance, doses from about 0.3 to about 3 mg/Kg s.c. of compounds representative of the invention are effective against *Staphylococcus aureus* infections in mice. The following examples illustrate the process of the invention and describe in detail some compounds of general formula I without limiting the scope of the invention.

EXAMPLE 1

4-deoxy-2′-[[(phenylmethoxy)imino]methyl]-thiazolo[5,4-c]-rifamycin.

4.1 ml of triethylamine, 900 mg of cysteine hydrochloride and 1.6 g of benzylhydroxylamine hydrochloride are added to a solution of 7 g of rifamycin S in 300 ml of methanol. After two hours at room temperature, the reaction mixture is taken to dryness under vacuum and the residue is purified by column chromatography (silica-gel Merck 0.05–0.20 mm, elutant CHCl₃:MeOH 98:2).

The fractions containing the pure compound are pooled and taken to dryness and the obtained compound is crystallized from ethyl acetate/petroleum ether. Yield 400 mg - M.P. 139°–140° C. (with decomposition).

| Elemental analysis | C | H | N | S |
|---|---|---|---|---|
| calculated for C₄₆H₅₃N₃O₁₂S | 63.36 | 6.13 | 4.82 | 3.68 |
| found | 63.48 | 6.45 | 4.96 | 3.55 |

| U.V. - visible absorption bands | (buffer pH 7.38) |
|---|---|
| $\lambda_{max}^{(nm)}$ | $E_{1cm}^{1\%}$ |
| 300 | 299 |
| 400 | 204 |

EXAMPLE 2

4-deoxy-2′-[[(piperidinyl)imino]methyl]thiazolo[5,4-c]-rifamycin.

1 g of cysteine and 1 ml of N-aminopiperidine are added at room temperature under stirring to a solution of 7 g of rifamycin S in 300 ml of methanol and 20 ml of buffer pH 4.6 (aqueous solution of citric acid and disodium phosphate). After 1 hour the reaction mixture is diluted with water, acidified and extracted with ethyl acetate. The organic phase is washed with a buffer solution to remove rifamycin SV, then anidrified and taken to dryness. The crude material thus obtained is purified by preparative chromatography, giving 1 g of pure compound M.p. 238°–40° C.

| Elemental analysis | C | H | N | S |
|---|---|---|---|---|
| calculated for C₄₄H₅₆N₄O₁₁S | 62.24 | 6.65 | 6.60 | 3.77 |
| found | 60.55 | 6.54 | 6.22 | 3.52 |

| U.V. - visible absorption bands | (buffer pH 7.38) |
|---|---|
| $\lambda_{max}^{(nm)}$ | $E_{1\,cm}^{1\%}$ |
| 226 | 488 |
| 276 | 288 |
| 320 | 275 |
| 405 | 276 |

EXAMPLE 3

4-deoxy-2′-[[(4-methyl-piperazinyl)imino]methyl]-thiazolo[5,4-c]rifamycin.

The compound of the title is prepared according to the procedure of the foregoing example but using N-amino-N′-methylpiperazine (1.6 ml) instead of N-aminopiperidine. Yield 450 mg. M.p. 180° C. (with decomposition).

| Elemental analysis | C | H | N | S |
|---|---|---|---|---|
| calculated for $C_{44}H_{57}N_5O_{11}S$ | 61.16 | 6.65 | 8.11 | 3.71 |
| found | 59.78 | 6.54 | 7.88 | 3.52 |

| U.V. - visible absorption bands | (buffer pH 7.38) |
|---|---|
| $\lambda max^{(nm)}$ | $E_{1\ cm}^{1\%}$ |
| 279 | 334 |
| 304 | 328 |
| 398 | 283 |

EXAMPLE 3 bis 4-deoxy-2'-[[(4-methyl-piperazinyl)imino]methyl]-thiazolo[5,4-c]rifamycin is also prepared according to a two-step procedure by adding 350 mg of manganese dioxide and 0.8 ml of N-amino-N'-methylpiperazine to a solution of 350 mg of 3-[(2-aminoethyl)thio]rifamycin in 15 ml of methanol and 1 ml of buffer pH 4.6, or by reacting a solution of 3-[(2-amino-carboxyethyl)thio]-rifamycin in methanol and buffer pH 4.6 with N-amino-N'-methylpiperazine in the presence of an equimolar amount of rifamycin S as the oxidizing agent.

The open-chained starting compounds can be easily prepared by reacting equimolar amounts of rifamycin S and cysteine or cysteamine in a water-miscible organic solvent.

EXAMPLE 4

4-deoxy-2'-[[(N,N-dimethyl)hydrazono]methyl]-thiazolo[5,4-c]rifamycin.

The compound of the title is prepared according to the procedure described in example 2 but using N,N-dimethylhydrazine (60 mg) instead of N-aminopiperidine. Yield 650 mg M.p. >172° C. (with decomposition).

| Elemental analysis | C | H | N | S |
|---|---|---|---|---|
| calculated for $C_{41}H_{52}N_4O_{11}S$ | 60.87 | 6.48 | 6.93 | 3.96 |
| found | 59.76 | 6.35 | 6.78 | 3.87 |

| U.V. - visible absorption bands | (buffer pH 7.38) |
|---|---|
| $\lambda max^{(nm)}$ | $E_{1\ cm}^{1\%}$ |
| 225 | 540 |
| 265 | 328 |
| 322 | 303 |
| 394 | 288 |

EXAMPLE 4 bis 4-deoxy-2'-[[(N,N-dimethyl)hydrazono]methyl]-thiazolo-[5,4-c]rifamycin is also prepared by reacting a dimethylsulfoxide solution of 3-[(2-aminoethyl)thio]-rifamycin with an aqueous solution of Potassium ferricyanide and dimethylhydrazine for about 15 minutes.

EXAMPLE 5

4-deoxy-2'-[(acetylhydrazono)methyl]thiazolo[5,4-c]-rifamycin.

800 mg of cysteine and 800 mg of acetohydrazide are added at room temperature, under stirring to a solution of 7 g of rifamycin S in 300 ml of methanol. After 4 hours, thin layer chromatography of the reaction mixture shows the disappearance of the starting rifamycin S, the presence of the yellow spot of the new product, the presence of rifamycin SV, besides trace-amount of by-products; the reaction mixture is taken to dryness under vacuum, dissolved in ethyl acetate and washed with buffer (pH 7.38); the buffered phase is acidified and extracted with ethyl acetate and the combined organic extracts are taken to dryness and further purified by column chromatography yielding 1 g of pure compound. M.p. 185°-7° C. (with decomposition).

| Elemental analysis | C | H | N | S |
|---|---|---|---|---|
| calculated for $C_{41}H_{50}N_4O_{12}S$ | 59.84 | 6.12 | 6.81 | 3.90 |
| found | 58.66 | 6.17 | 6.52 | 3.60 |

| U.V. - visible absorption bands | (buffer pH 7.38) |
|---|---|
| $\lambda max^{(nm)}$ | $E_{1\ cm}^{1\%}$ |
| 225 | 581 |
| 295 | 381 |
| 408 | 286 |

By operating according to the procedure of the foregoing examples, the following compounds are obtained:

4-deoxy-2'-[[(methoxy)imino]methyl]thiazolo[5,4-c]rifamycin 4-deoxy-2'-[[(ethoxy)imino]methyl]thiazolo[5,4-c]rifamycin 4-deoxy-2'-[[(propyloxy)imino]methyl]thiazolo[5,4-c]rifamycin 4-deoxy-2'-[[(butyloxy)imino]methyl]thiazolo[5,4-c]rifamycin 4-deoxy-2'-[[(pentyloxy)imino]methyl]thiazolo[5,4-c]rifamycin 4-deoxy-2'-[[(2-hydroxy-ethoxy)imino]methyl]-thiazolo[5,4-c]rifamycin 4-deoxy-2'-[[(octyloxy)imino]methyl]thiazolo[5,4-c]rifamycin 4-deoxy-2'-[[(1-carboxy-2-methyl-propyloxy)imino]-methyl]thiazolo[5,4-c]rifamycin 4-deoxy-2'-[[(2-phenylethoxy)imino]methyl]-thiazolo[5,4-c]rifamycin 4-deoxy-2'-[[(3-phenyl-propyloxy)imino]methyl]-thiazolo[5,4-c]-rifamycin 4-deoxy-2'-[[((2,4-dichlorophenyl)methoxy)imino]-methyl]thiazolo[5,4-c]rifamycin 4-deoxy-2'-[[(1-propyl-butoxy)imino]methyl]-thiazolo[5,4-c]rifamycin 4-deoxy-2'-[[(4-pentenyloxy)imino]methyl]-thiazolo[5,4-c]rifamycin 4-deoxy-2'-[[(2-ethylpropenyloxy)imino]methyl]-thiazolo[5,4-c]rifamycin 4-deoxy-2'-[[(2-propenyloxy)imino]methyl]-thiazolo[5,4-c]rifamycin 4-deoxy-2'-[[(2-propynyloxy)imino]methyl]-thiazolo[5,4-c]rifamycin 4-deoxy-2'-[[(2-phenoxy-ethoxy)imino]methyl]-thiazolo[5,4-c]rifamycin 4-deoxy-2'-[[(1-ethylpentyloxy)imino]methyl]-thiazolo[5,4-c]rifamycin 4-deoxy-2'-[[(tricyclopentylmethoxy)imino]methyl]-thiazolo[5,4-c]rifamycin 4-deoxy-2'-[[(cyclopentyloxy)imino]methyl]-thiazolo[5,4-c]rifamycin 4-deoxy-2'-[[(2-propyloxy-ethoxy)imino]methyl]-thiazolo[5,4-c]rifamycin 4-deoxy-2'-[[((2-dimethylamino)ethoxy)imino]methyl]thiazolo[5,4-c]rifamycin 4-deoxy-2'-[[((2-diethylamino)ethoxy)imino]methyl]-thiazolo[5,4-c]rifamycin 4-deoxy-2'-[[((2-methylamino)ethoxy)imino]methyl]-thiazolo[5,4-c]rifamycin 4-deoxy-2'-[[(cycloheptyloxy)imino]methyl]-thiazolo[5,4-c]rifamycin 4-deoxy-2'-[[(1-piperazinyl)imino]methyl]-thiazolo[5,4-c]rifamycin
4-deoxy-2'-[[(4-morpholinyl)imino]methyl]-thiazolo[5,4-c]rifamycin
4-deoxy-2'-[[(1-pyrrolidinyl)imino]methyl]-thiazolo[5,4-c]rifamycin
4-deoxy-2'-[[(4-cyclopentyl-1-piperazinyl)imino]methyl]thiazolo[5,4-c]rifamycin
25-desacetyl-4-deoxy-2'-[[(phenylmethoxy)imino]methyl]thiazolo[5,4-c]rifamycin
25-desacetyl-4-deoxy-2'-[[(methoxy)imino]methyl]-thiazolo[5,4-c]rifamycin
25-desacetyl-4-deoxy-2'-[[(4-pentenyloxy)imino]methyl]thiazolo[5,4-c]rifamycin
25-desacetyl-4-deoxy-2'-[[(octyloxy)imino]methyl]-thiazolo[5,4-c]rifamycin
25-desacetyl-4-deoxy-2'-[[(1-piperidinyl)imino]methyl]thiazolo[5,4-c]rifamycin
25-desacetyl-4-deoxy-2'-[[(1-piperazinyl)imino]methyl]thiazolo[5,4-c]rifamycin
25-desacetyl-4-deoxy-2'-[[(4-methyl-1-piperazinyl)imino]methyl]thiazolo[5,4-c]rifamycin
25-desacetyl-4-deoxy-2'-[[(4-cyclopentyl-1-piperazinyl)imino]methyl]thiazolo[5,4-c]rifamycin
4-deoxy-2'-[[(cyclopentyl)hydrazono]methyl]-thiazolo[5,4-c]rifamycin
4-deoxy-2'-[[(cyclohexyl)hydrazono]methyl]-thiazolo[5,4-c]rifamycin
4-deoxy-2'-[[(2-diethylamino)ethyl)hydrazono]methyl]thiazolo[5,4-c]rifamycin
4-deoxy-2'-[[(phenyl)hydrazono]methyl]thiazolo[5,4-c]rifamycin
4-deoxy-2'-[[(cyclooctyl)hydrazono]methyl]-thiazolo[5,4-c]rifamycin
4-deoxy-2'-[[(cycloheptyl)hydrazono]methyl]-thiazolo[5,4-c]rifamycin
4-deoxy-2'-[[(phenylmethyl)hydrazono]methyl]-thiazolo[5,4-c]rifamycin
4-deoxy-2'-[[(3-methyl-phenyl)hydrazono]methyl]-thiazolo[5,4-c]rifamycin
4-deoxy-2'-[[(2,4-dinitrophenyl)hydrazono]methyl]-thiazolo[5,4-c]rifamycin
4-deoxy-2'-[[(2-propenyl)hydrazono]methyl]-thiazolo[5,4-c]rifamycin
4-deoxy-2'-[[(2-phenoxyethyl)hydrazono]methyl]-thiazolo[5,4-c]rifamycin
4-deoxy-2'-[[(N,N-di(2-diethylaminoethyl)hydrazono]methyl]thiazolo[5,4-c]rifamycin
4-deoxy-2'-([[(2-(4-amino-2,6-dichlorophenoxy)ethyl)hydrazono]methyl]thiazolo[5,4-c]rifamycin
4-deoxy-2'-[[(2-methylphenyl)hydrazono]methyl]-thiazolo[5,4-c]rifamycin
4-deoxy-2'-[[(4-fluorophenyl)hydrazono]methyl]-thiazolo[5,4-c]rifamycin
4-deoxy-2'-[[(N-butyl-N-methyl)hydrazono]methyl]-thiazolo[5,4-c]rifamycin
4-deoxy-2'-[[(4-(α,αdimethylethyl)-2,6-dimethylphenyl)hydrazono]methyl]thiazolo[5,4-c]rifamycin
4-deoxy-2'-[[(N,N-dioctyl)hydrazono]methyl]-thiazolo[5,4-c]rifamycin
4-deoxy-2'-[[(2-ethoxyphenyl)hydrazono]methyl]-thiazolo[5,4-c]rifamycin
4-deoxy-2'-[[(propanoyl)hydrazono]methyl]-thiazolo[5,4-c]rifamycin
4-deoxy-2'-[[(2-methylpropanoyl)hydrazono]methyl]thiazolo[5,4-c]rifamycin
4-deoxy-2'-[[(3-phenylpropanoyl)hydrazono]methyl]thiazolo[5,4-c]rifamycin
4-deoxy-2'-[[(4-(2-methyl-propyl)benzoyl)hydrazono]methyl]thiazolo[5,4-c]rifamycin
4-deoxy-2'-[[(3,5-dimethoxy-benzoyl)hydrazono]methyl]thiazolo[5,4-c]rifamycin
4-deoxy-2'-[[(4-aminobenzoyl)hydrazono]methyl]-thiazolo[5,4-c]rifamycin
4-deoxy-2'-[[(benzoyl)hydrazono]methyl]-thiazolo[5,4-c]rifamycin
4-deoxy-2'-[[(cyanoacetyl)hydrazono]methyl]-thiazolo[5,4-c]rifamycin
4-deoxy-2'-[[(2-amino-3-(4-hydroxyphenyl)-propanoyl)hydrazono]methyl]thiazolo[5,4-c]rifamycin
4-deoxy-2'-[[(2-methoxy-benzoyl)hydrazono]methyl]thiazolo[5,4-c]rifamycin
25-desacetyl-4-deoxy-2'-[[(ciclopentyl)hydrazono]methyl]thiazolo[5,4-c]rifamycin
25-desacetyl-4-deoxy-2'-[[(cyclohexyl)hydrazono]methyl]thiazolo[5,4-c]rifamycin
25-desacetyl-4-deoxy-2'-[[(butyl)hydrazono]methyl]-thiazolo[5,4-c]rifamycin

We claim:

1. A process for preparing a 4-desoxy-thiazolo[5,4-c]rifamycin of the formula

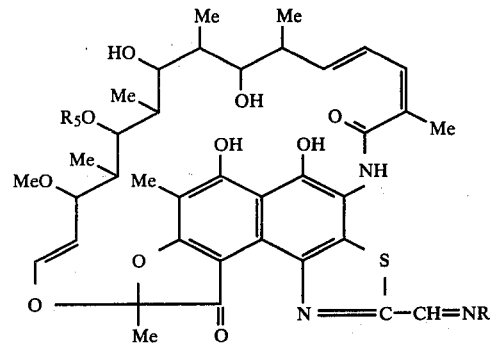

wherein R stands for a group —OR$_1$, or —NH—CO—R$_4$ wherein R$_1$ represents alkyl having 1 to 8 carbon atoms per group and no substitution or halo, amino, mono- or di- (C$_{1-4}$) alkylamino, C$_{1-4}$ alkoxy, C$_{5-8}$ cycloalkoxy, phenoxy phenyl (C$_{1-4}$) alkoxy, nitro, cyano, hydroxy, carboxy, carbo (C$_{1-4}$) alkoxy or carbamoyl substitution; alkenyl having up to 8 carbon atoms per group which contains one or two double bonds, alkynyl having up to 8 carbon atoms per group which contains one or two triple bonds, cycloalkyl having a cycloaliphatic ring containing from 5 to 8 carbon atoms and having up to two C$_{1-4}$ alkyl substituents, aryl or aralkyl wherein aryl as such or in a compound term designates phenyl or phenyl having halo, C$_{1-4}$ alkyl, halo (C$_{1-4}$) alkyl, C$_{1-4}$ alkenyl, C$_{5-8}$ cycloalkyl, amino, mono- or di- (C$_{1-4}$) alkylamino, C$_{1-4}$ alkoxy, methylenedioxy, cyano, carboxy, hydroxy, carbo (C$_{1-4}$) alkoxy, carbamoyl or nitro substitution, R$_2$ and R$_3$ are independently selected from hydrogen, alkyl, alkenyl, alkynyl, cycloalkyl, aryl and aralkyl, as defined above, or R$_2$ and R$_3$ taken together with the adjacent nitrogen atom may form a 5–7 membered heterocyclic ring wherein the hetero atoms are nitrogen, and R$_5$ is hydrogen or acetyl;

which comprises reacting rifamycin S or its 25-desacetyl derivative with a cysteine derivative of formula III

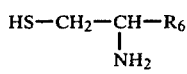

wherein R₆ stands for —H or —COOH in a water-miscible organic solvent, at a temperature comprised between room temperature and the boiling temperature of the reaction mixture whereby a 3-[(2-substituted ethyl)thio]rifamycin derivative of formula V

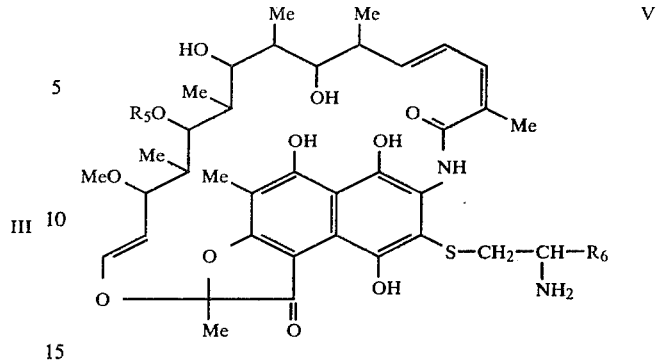

is obtained wherein $R_5$ and $R_6$ are as defined before, and contacting said derivative with about a equimolar amount of a compound of formula H₂NR wherein R is as defined before and at least the stoichiometric amount of an oxidizing agent.

2. A process as in claim 1 wherein the oxidizing agent is selected from p-quinone, 2,5-dimethyl-p-quinone, 2,6-dimethoxy-p-quinone, tetrachloro-p-quinone, dichlorodicyano-p-quinone, duroquinone, rifamcyin S, alkyl nitrites, hydrogen peroxide, alkali metal persulfates, alkali metal ferricyanides, cupric acetate, mercuric acetate and manganese dioxide.

3. A process as in claim 1 wherein the reaction between rifamycin S derivative and the cysteine derivative and the subsequent contacting of the obtained 3-(2-substituted ethylthio)rifamycin derivative with a compound of formula H₂NR and an oxidizing agent is performed in a single operation step.

4. A process as in claim 3 wherein the oxidizing agent is selected from tetrasubstituted quinones and rifamycin S.

* * * * *